United States Patent [19]

Ozaki

[11] Patent Number: 5,699,399
[45] Date of Patent: Dec. 16, 1997

[54] X-RAY COMPUTED TOMOGRAPHY APPARATUS

[75] Inventor: Masahiro Ozaki, Otawara, Japan

[73] Assignee: Kabushiki Kaisha Toshiba, Kawasaki, Japan

[21] Appl. No.: 593,376

[22] Filed: Jan. 29, 1996

[30] Foreign Application Priority Data

Jan. 31, 1995 [JP] Japan .................................. 7-014047

[51] Int. Cl.$^6$ .................................................. H05G 1/64
[52] U.S. Cl. ........................ 378/4; 378/98.2; 378/98
[58] Field of Search .............................. 378/4, 62, 98.5, 378/98, 98.2, 98.8

[56] References Cited

U.S. PATENT DOCUMENTS 5,440,607  8/1995  Nakaya .......................... 378/98.5

*Primary Examiner*—Don Wong
*Attorney, Agent, or Firm*—Oblon, Spivak, McClelland, Maier & Neustadt, P.C.

[57] ABSTRACT

An X-ray computed tomography apparatus including a scanner for scanning a subject with X-rays to repeatedly acquire projection data items, real-time operating unit for sequentially reconstructing image items based on the acquired projection data items, and dynamically displaying reconstructed image items along a forward direction of the time axis, with an acquisition of the projection data items, storage for storing the acquired projection data items with time information, and playback device for sequentially reconstructing image items based on the read projection data times from the storage, and dynamically displaying reconstructed image items along a reserve direction of the axis based on the time information, when the acquision of the projection data items is stored.

9 Claims, 4 Drawing Sheets

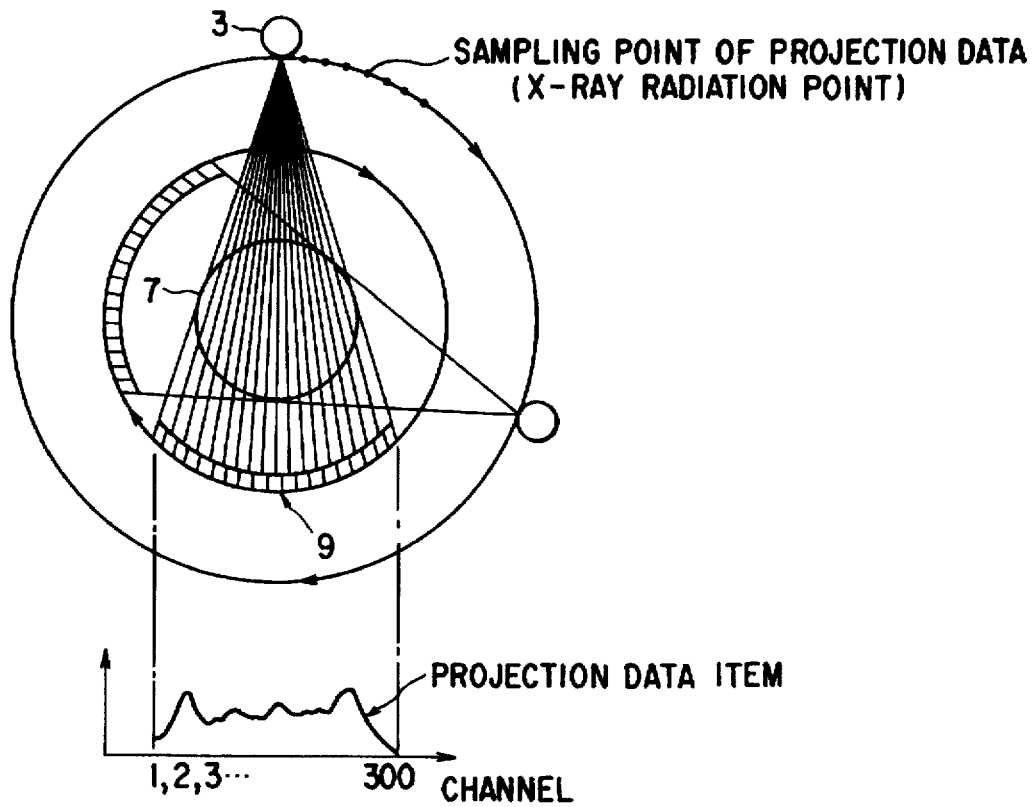
F I G. 2
F I G. 4

X-RAY COMPUTED TOMOGRAPHY APPARATUS

BACKGROUND OF THE INVENTION

1. Field of the Invention

The present invention relates to an X-ray computed tomography apparatus, which is capable of executing a CT-fluoroscopic operation wherein a cross section of an examined object is repeatedly scanned with X-rays, projection data for a cross-sectional image is repeatedly reconstructed based on projection data during the scanning, and the cross-sectional image is displayed as a dynamic image.

2. Description of the Related Art

The CT-fluoroscopic technique is based on high-speed reconstruction processing using a high-speed processor and a parallel distributed processing. In the CT-fluoroscopic operation, it is needed that a time, which is required to reconstruct one cross-sectional image, be shorter than a time, which is required to acquire projection data items for 360° when reconstructing the cross-sectional image of one frame.

In this case, "projection data item" is defined as n numbers of detected data items detected by an n-channel type X-ray detector due to one X-ray radiation. Also, "scan" is defined as an operation for sequentially acquiring projection data items.

In a console of the X-ray computed computed tomography apparatus, which is capable of executing a CT-fluoroscopic operation, there is provided a scan stop button, which is operated by an operator. If the scan stop button is pressed, X-ray radiation is stopped.

The operator observes a dynamic image on the CT-fluoroscopic operation, and presses the scan stop button when a suitable cross-sectional image is displayed.

When the scan stop button is pressed, projection data items for, e.g., 10 seconds, are stored in a memory of the X-ray computed tomography apparatus. When the scan stop button is pressed, the projection data items are sequentially read from the memory to a reconstruction unit in order of old data in accordance with acquisition of data.

The reconstruction unit repeatedly reconstructs the cross-sectional image based on the projection data items sent from the memory. The reconstructed cross-sectional image is played back as a dynamic image in a forward direction on a time axis. The operator confirms a suitable cross-sectional image based on the played back dynamic image.

However, there is a problem in that an extremely long wait time is needed until the suitable cross-sectional image is displayed after the start of the playback operation.

SUMMARY OF THE INVENTION

An object of the present invention is to provide an X-ray computed tomography apparatus, which can reduce wait time until a suitable cross-sectional image is displayed after the end of a CT-fluoroscopic operation.

According to the present invention, there can be provided an X-ray computed tomography apparatus comprising scanning means for scanning a subject with X-rays to repeatedly acquire projection data items; real-time operating means for sequentially reconstructing image items based on the acquired projection data items, and dynamically displaying reconstructed image items along a forward direction of the time axis, with an acquisition of the projection data items; storing means for storing the acquired projection data items with time information; and playback operating means for sequentially reconstructing image items based on the read projection data times from the storing means, and dynamically displaying reconstructed image items along a reserve direction of the axis based on the time information, when the acquisition of the projection data items is stored.

Also, according to the present invention, there can be provided an X-ray computed tomography apparatus comprising scanning means for scanning a subject with X-rays to repeatedly acquire projection data items; real-time operating means for sequentially reconstructing image items based on the acquired projection data items, and dynamically displaying reconstructed image items along a forward direction of the time axis, with an acquisition of the projection data items; storing means for storing the image data items with time information; and playback operating means for dynamically displaying the read image data items from the storing means along a reverse direction of the time axis and on the same time scale as the acquisition time based on the time information when the acquisition of the projection data items is stopped.

After the scan is stopped, the dynamic image is reproduced in a reverse direction. Therefore, there can be reduced wait time until an important cross-sectional image just before the scan stop is displayed.

Additional objects and advantages of the invention will be set forth in the description which follows, and in part will be evident from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

FIG. 2 is a view showing one example of projection data;

FIG. 4 is a view showing projection data stored in a projection data memory of FIG. 1 and attribute data.

DETAILED DESCRIPTION OF THE PREFERRED EMBODIMENTS

The following will explain a preferable embodiment of the present invention with reference to the drawings.

In this case, an X-ray computed tomography apparatus will be explained as a rotate/rotate(R/R)-type X-ray computed tomography apparatus. However, the X-ray computed tomography apparatus of this embodiment is not limited to the R/R-type X-ray computed tomography apparatus. In the X-ray computed tomography apparatus of this embodiment, stationary/rotate(S/R)-type or the other type may be used. The R/R-type X-ray computed tomography apparatus comprises an X-ray tube and an X-ray detector, which rotate around an examining object as one unit. In the S/R-type X-ray computed tomography apparatus, 600 to 2000 X-ray detecting elements are circumferentially fixed, and the X-ray tube rotates around the examining object.

The "projection data items" used in the below are defined as n numbers of detected data items, which are simultaneously acquired by an n X-ray detecting elements which an n channel type X-ray detector has. Also, the "image data items" are defined as one group of pixel data items forming one frame. Moreover, "scan" is defined as an operation for continuously acquiring the projection data item.

Figure 1:
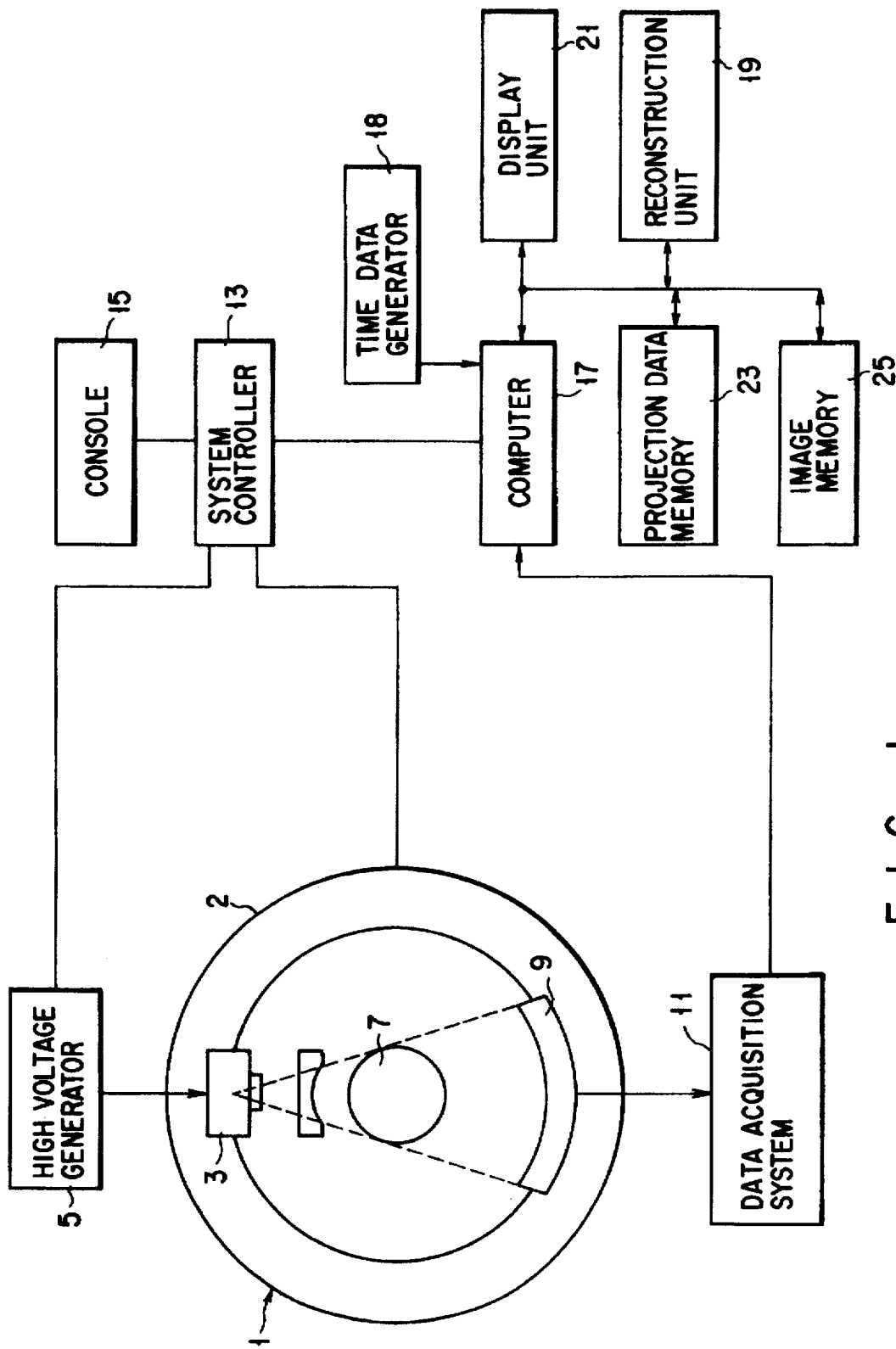
FIG. 1 is a structural view of an X-ray computed tomography apparatus of a preferable embodiment of the present invention.

FIG. 1 shows the structure of the X-ray computed tomography apparatus according to one embodiment of the present invention. A gantry 1 contains an X-ray tube 3 and an n channel X-ray detector 9. The X-ray tube 3 generates a fan X-ray beam having a width wide enough to cover an imaging area 7. The X-ray tube is attached to a rotation ring 2. An n channel X-ray detector 9 has a plurality of X-ray detecting elements, which are circularly arrayed. In this case, one X-ray detecting element corresponds to one channel. The n channel X-ray detector 9 is attached to the rotation ring 2 at a position, which sandwiches the image area 7 to be opposite to the X-ray tube 3.

A high voltage generator 5 periodically applies a pulse high voltage to the X-ray tube 3 in order to periodically radiate pulse X-ray.

Each of the plurality of X-ray detecting elements of the n channel X-ray detector 9 converts X-ray, which is passed through the examining object provided to the imaging area 7, to a weak electrical signal.

A data acquisition system 11 individually amplifies the electrical signals detected by the X-ray detecting elements, and A/D-converts the signals, thereby periodically acquiring a projection data item. The projection data item is supplied to a slip ring (not shown) through a computer 17.

The computer 17 transfers the projection data item to a reconstruction unit 19 and a projection data memory 23 from the data acquisition system 11.

The reconstruction unit 19 comprises a parallel high-speed processor in order to realize a CT-fluoroscopic operation. The reconstruction unit 19 reconstructs an image data item (cross-sectional image) based on the projection data items for 360°. The reconstruction unit 19 supplies the image data item to a display unit 21 and an image memory 25.

A time data generator 18 repeatedly supplies a time data item to the computer 17. The time data item shows an actual time or the passage of time since the start of scanning. The computer 17 transfers the time data time to a projection data memory 23. The time data item, which is transferred to the projection data memory from the computer 17, corresponds to time in which projection data times are acquired or the passage of time.

Also, the computer 17 transfers the time data item to an image memory 25. Similarly, the time data item corresponds to time in which projection data times are acquired to reconstruct the image data item or the passage of time.

The projection data memory 23 stores projection data items sent from the computer 17 and time data items, which correspond to projection data items, respectively. The projection data memory 23 has a storage capacity necessary for storing the projection data items acquired by scanning for, e.g., 10 seconds and time data items.

The display unit 21 dynamically displays the cross-sectional image based on a series of image data items sent from the reconstruction unit 19 or the image memory 25.

The image memory 25 stores the image data items sent from the reconstruction unit 19 and the time data items, which correspond to the image data items, respectively. The image memory 25 has a storage capacity sufficient to store the projection data items acquired by scanning for, e.g., 10 seconds and time data items.

A system controller 13 supplies a control signal to a drive system of a rotation ring 2 (not shown) in order to rotate the rotation ring 2 by one second/cycle. The system controller 13 supplies a control signal to the high voltage generator 5 every time when the rotation ring rotates by 10° in order to periodically radiate X-ray. The system controller 13 supplies the control signal to the data acquisition system 11 so as to periodically detect X-ray to be synchronized with periodic radiation of X-ray.

A console 15 is connected to the system controller 13. The console 15 has a scan stop button by which an operator intentionally stops the CT-scanning.

An operation of this embodiment will be explained as follows.

First, a scanning operation will be explained.

FIG. 2 is a view explaining the scanning operation. The rotation ring 2 rotates at the speed of one second/cycle. Every time when the rotation ring 10 rotates by 10°, X-ray is radiated from the X-ray tube 3, and the projection data items are periodically acquired by the data acquisition system 11 to be synchronized with the radiation of X-ray. The acquisition period of the projection data items is shown by "C." There is a possibility that the acquisition period C will be slightly varied by unstable radiation period of X-ray.

Next, the CT scanning will be explained. The CT scanning means that the cross-sectional image is rapidly and repeatedly reconstructed in parallel with the scanning so as to display the cross-sectional image as a dynamic image.

Figure 3:
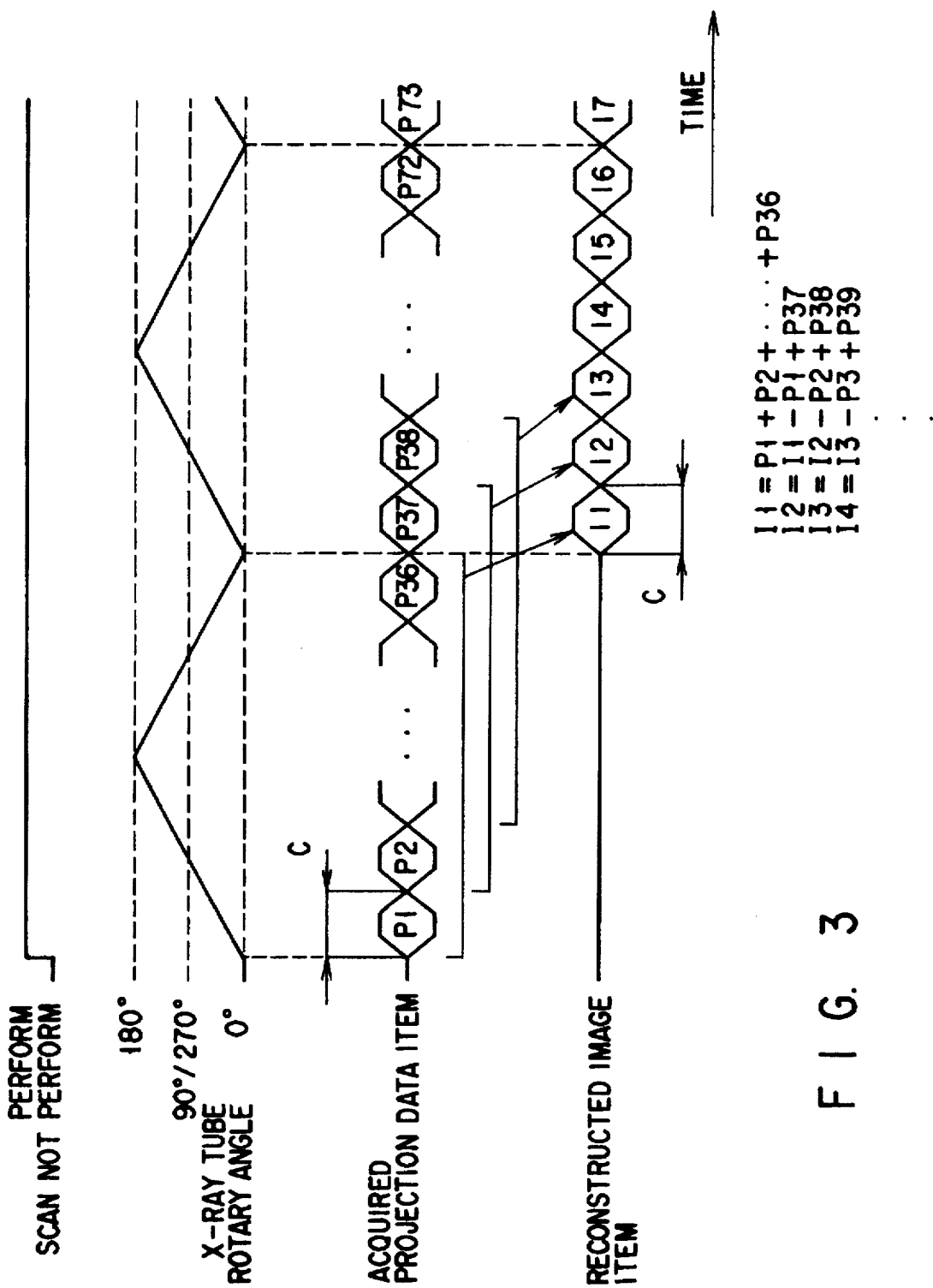
FIG. 3 is a time chart of a CT-fluoroscopic operation

FIG. 3 is a time chart of a CT scanning operation. In this time chart, time delay of mainly the reconstruction structure is shown by "0". The projection data items P are repeatedly acquired by period C.

In the stage when projection data items P1 to P36 for 360° are arranged, a first image data item I1 is reconstructed by the reconstruction unit 19 after the start of the scanning. The first image data item I1 is sent to the display unit 21 to be displayed.

When a first projection data item P37 of a second period is acquired, a second image data I2 is reconstructed by the reconstruction unit 19 after the start of the scanning. The second image data item I2 is sent to the display unit 21 to be displayed in place of the first image data item I1.

The second image data item I2 is reconstructed based on the image data item I1, which is reconstructed one period before, projection data item P1, which is the oldest among the projection data items P1 to P36 used in the reconstruction of the image data item I1, and the latest projection data item P37. The oldest projection data item P1 is supplied to a back projection processing in a reverse direction of the image data item I1. The latest projection data item P37 is supplied to the back projection processing in a forward direction of the first image data item I1. In this figure, the back projection processing of the reverse direction is shown by (−), and the the back projection processing of the forward direction is shown by (+). Such partial reconstruction processing is one processing technique for improving the high-speed operation and time resolution, and the present invention is not limited to such a technique.

As mentioned above, the projection data items P are periodically acquired by period C. Also, the image data items I are periodically reconstructed by the same period C.

The image data items I are displayed as a dynamic image in the forward direction to the time axis.

The following will explain an operation when the CT scanning is stopped.

Figure 5:
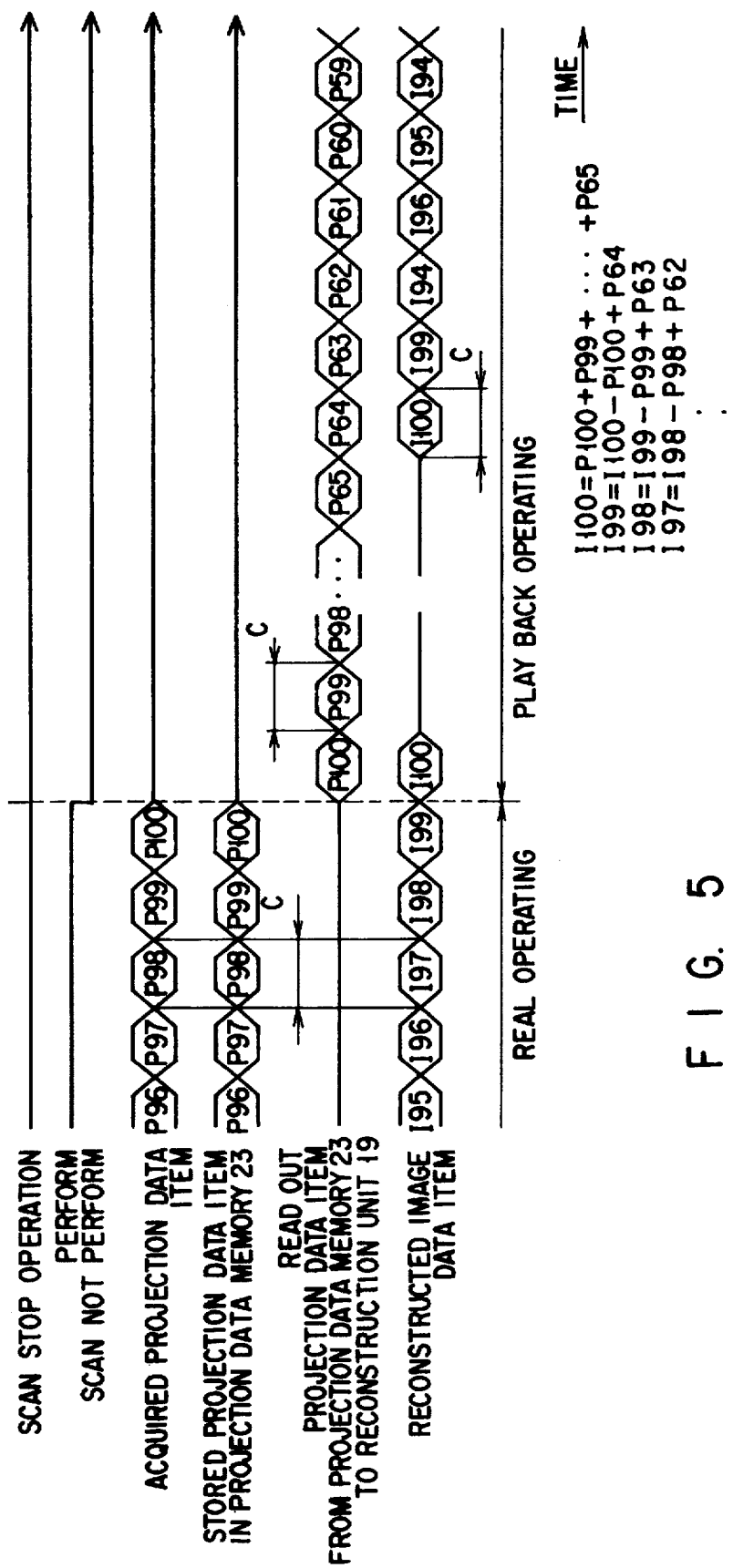
FIG. 5 is a time chart of an operation when the CT-fluoroscopic operation is stopped.

FIG. 5 is a time chart of the operation when the CT scanning is stopped.

While the CT scanning is continued, the projection data items periodically acquired are sent to the projection data memory 23 from the computer 17, and sequentially stored in the projection data memory 23 together with the corresponding data items as shown in FIG. 4.

If the CT scanning is continued for more than 10 seconds, the projection data memory 23 is in a full state. The projection data memory 23 erases the oldest projection data item, and writes the latest projection data item. Thereby, the latest data items corresponding to 10 seconds are always stored in the projection data memory 23.

If the operator presses the scan stop button of the console 15, the rotation of the rotation ring 2 and radiation of X-ray are stopped. Thereby, the scanning is stopped. When the scanning is stopped, the projection data items P1 to P100 are stored in the projection data memory 23.

When the scanning is stopped, the computer 17 sequentially reads the respective data items P1 to P100 in order of the latest data item to the reconstruction unit 19 from the projection data memory 23 by period C based on the time data times.

In this case, if the acquisition period C of the projection data items is varied at the time of scanning, the computer 17 varies the period of which each of the projection data items P1 to P100 is read to the reconstruction unit 19 from the projection data memory 23 in accordance with the varied acquisition period C. Thereby, the projection data items can be supplied to the reconstruction unit 19 in the order, which is opposite to the case of the scanning time, on the same time scale as time scale used when the projection data items P1 to P100 were acquired at the scanning time.

After the scanning is stopped, the latest projection data item P100 is first supplied to the reconstruction unit 19 from the projection data memory 23. Next, the projection data item P99, which was acquired one period before the projection data item P100, is supplied to the reconstruction unit 19 from the projection data memory 23. In this way, the respective projection data items P1 to P100 are supplied to the reconstruction unit 19 in order of the latest data.

In the stage when projection data items P100 to P65 for 360° are arranged, a first image data item I100 is reconstructed by the reconstruction unit 19 after the stop of the scanning. The first image data item I100 is sent to the display unit 21 to be displayed. The image data item I100, which is first reconstructed and displayed after the stop of the scanning, is the same as the image data item which is finally reconstructed on the CT-fluoroscopic operation and displayed.

When the projection data item P64 is supplied to the reconstruction unit 19, the second image data item I99 is reconstructed by the reconstruction unit 19 after the stop of the scanning. The second image data item I99 is sent to the display unit 21, and displayed in place of the first image data item I100.

In this way, the projection data items P are supplied to the reconstruction unit 19 in the order, which is opposite to the case of the acquisition time, on the same time scale as the case of the acquision time. Due to this, the dynamic image is reproduced in the reverse direction in the same scale as the case of the CT scanning time after the stop scan.

Thereby, there can be realized the technical advantage in which wait time, which is from the time when the scanning is stopped until the important cross-sectional image displayed just before the scan stop appears on the monitor can be reduced. In a conventional system, the dynamic image is reproduced in the same forward direction as the case of the CT scanning when the scanning is stopped. Therefore, wait time until the important cross-sectional image appeared on the monitor was a time related to the storage capacity of the memory, for example, about 10 seconds. However, according to the present invention, since the dynamic image is reproduced in the opposite direction when the scanning is stopped, wait time can be reduced to be within one second.

The embodiment of the present invention can be modified as follows.

More specifically, when the CT scanning is continued, the image memory 25 stores the image data items, which are sequentially reconstructed by the reconstruction unit 19, and the time data times, which correspond to the respective image data items. After the scan stop, the computer 17 supplies the respective image data items I1 to I100 to the display unit 21 from the image data memory 25 in the order, which is opposite to the order when the data items are reconstructed at the time of CT scanning, by the same fixed period C, which is the same as the case when the data items are reconstructed at the time of CT scanning, based on the time data items. The display unit 21 supplies the supplied image data items to the reconstruction unit 19 from the projection data memory 23 in the order, which is opposite to the order of the CT scanning time, by the fixed period C, which is the same as the acqustion time. However, as comparing the projection data items with the image data items, the amount of data of the projection data items is considerably smaller than that of the image data items. In view of this point, it is advantageous to store the projection data items.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An X-ray computed tomography apparatus comprising:
    scanning means for scanning a subject with X-rays to repeatedly acquire projection data items;
    real-time operating means for sequentially reconstructing image items based on the acquired projection data items, and dynamically displaying reconstructed image items along a forward direction of the time axis, with the scanning;
    storing means for storing the acquired projection data items with time information with the scanning;
    stopping means for stopping the scanning; and
    playback operating means for sequentially reconstructing image items based on the read projection data times from said storing means, and dynamically displaying reconstructed image items along a reverse direction of the axis based on the time information, after the scanning is stopped.

2. The apparatus according to claim 1, wherein said storing means stores each of the projection data items with a time data item corresponding to the time which each of the projection data items is acquired.

3. The apparatus according to claim 1, wherein said playback operating means sequentially displays said reconstructed image items on the same time scale as said real-time operating means.

4. The apparatus according to claim 1, wherein said storing means supplies said projection data items to said playback operating means in an opposite order on the same time scale as the case of the acquisition time.

5. The apparatus according to claim 1, wherein said playback operating means sequentially reconstructs said image items in order opposite to the case of the acquisition time.

6. The apparatus according to claim 1, wherein said storing means sequentially supplies said projection data items to said playback operating means in order opposite to the case of the acquisition time based on the time information, and said playback operating means sequentially reconstructs said image data items in order opposite to the case of the acquisition time by use of said projection data items in order of supplying from said storing means.

7. An X-ray computed tomography apparatus comprising:

scanning means for scanning a subject with X-rays to repeatedly acquire projection data items;

real-time operating means for sequentially reconstructing image items based on the acquired projection data items, and dynamically displaying reconstructed image items along a forward direction of the time axis, with the scanning;

storing means for storing the image data items with time information, with the scanning;

stopping means for stopping the scanning; and playback operating means for dynamically displaying the read image data items from said storing means along a reverse direction of the time axis and on the same time scale as the acquisition time based on the time information, after the scanning is stopped.

8. The apparatus according to claim 7, wherein said storing means stores each of the image data items with a time data item corresponding to the time which the projection data item used in reconstructing each of the image data items is acquired.

9. The apparatus according to claim 7, wherein said storing means supplies the image data items to said playback operating means in the opposite order on the same time scale as the case of the acquisition time.

* * * * *